United States Patent [19]

Rahat et al.

[11] Patent Number: 5,098,370

[45] Date of Patent: Mar. 24, 1992

[54] HEART ASSIST DEVICE

[75] Inventors: Shumel Rahat, Haifa; Joe Borman, Jerusalem; Dan Rottenberg, Haifa; Gideon Uretzky, Jerusalem, all of Israel

[73] Assignee: Galram Technology Industries, Inc., Haifa, Israel

[21] Appl. No.: 504,472

[22] Filed: Apr. 4, 1990

[30] Foreign Application Priority Data

Jan. 29, 1988 [IL] Israel ........................................ 85249

[51] Int. Cl.$^5$ ............................................ A61N 1/362
[52] U.S. Cl. ..................................................... 600/16
[58] Field of Search ................... 600/18, 16, 17; 623/3

[56] References Cited

U.S. PATENT DOCUMENTS

| | | | |
|---|---|---|---|
| 3,457,909 | 7/1969 | Laird | 600/17 |
| 4,583,525 | 4/1986 | Suzuki et al. | 600/16 |
| 4,796,606 | 1/1989 | Mushika | 623/3 |
| 4,934,996 | 6/1990 | Mohl et al. | 600/17 |

Primary Examiner—Francis Jaworski
Assistant Examiner—George Manuel
Attorney, Agent, or Firm—Browdy and Neimark

[57] ABSTRACT

There is provided a heart assist system aimed at saving lives of patients who's heart is failing temporarily. The assist system comprises means for continuously monitoring the hemodynamic parameter which define the demand of the body for blood to be circulated by the heart, means to define the heart's actual performance and provides means to draw the excess blood not provided by the failing heart at that beat. That blood is reintroduced during the systolic phase of the same beat. Thus the system establishes the supply of blood required, which is supplied at rate and at a shape as close as possible to that expected by the body. The main parameter monitored is the entire atrial pressure function during the diastolic phase of the heart beat which provides the indication of the real time heart performance thus making it possible to define and provide the required assistance to be provided by the system of the invention.

6 Claims, 7 Drawing Sheets

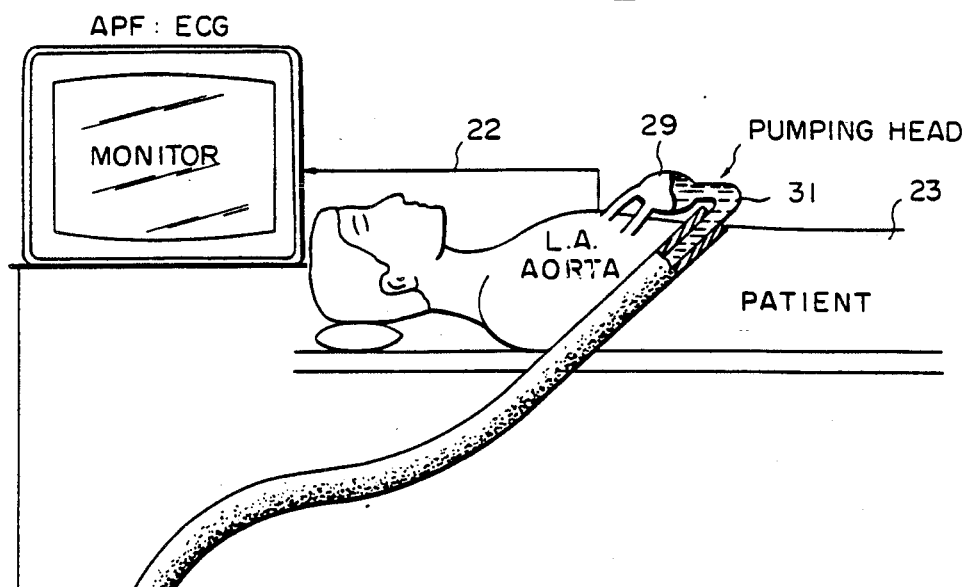

ASSIST MODE

BY-PASS AND COUNTER PULSATION MODE

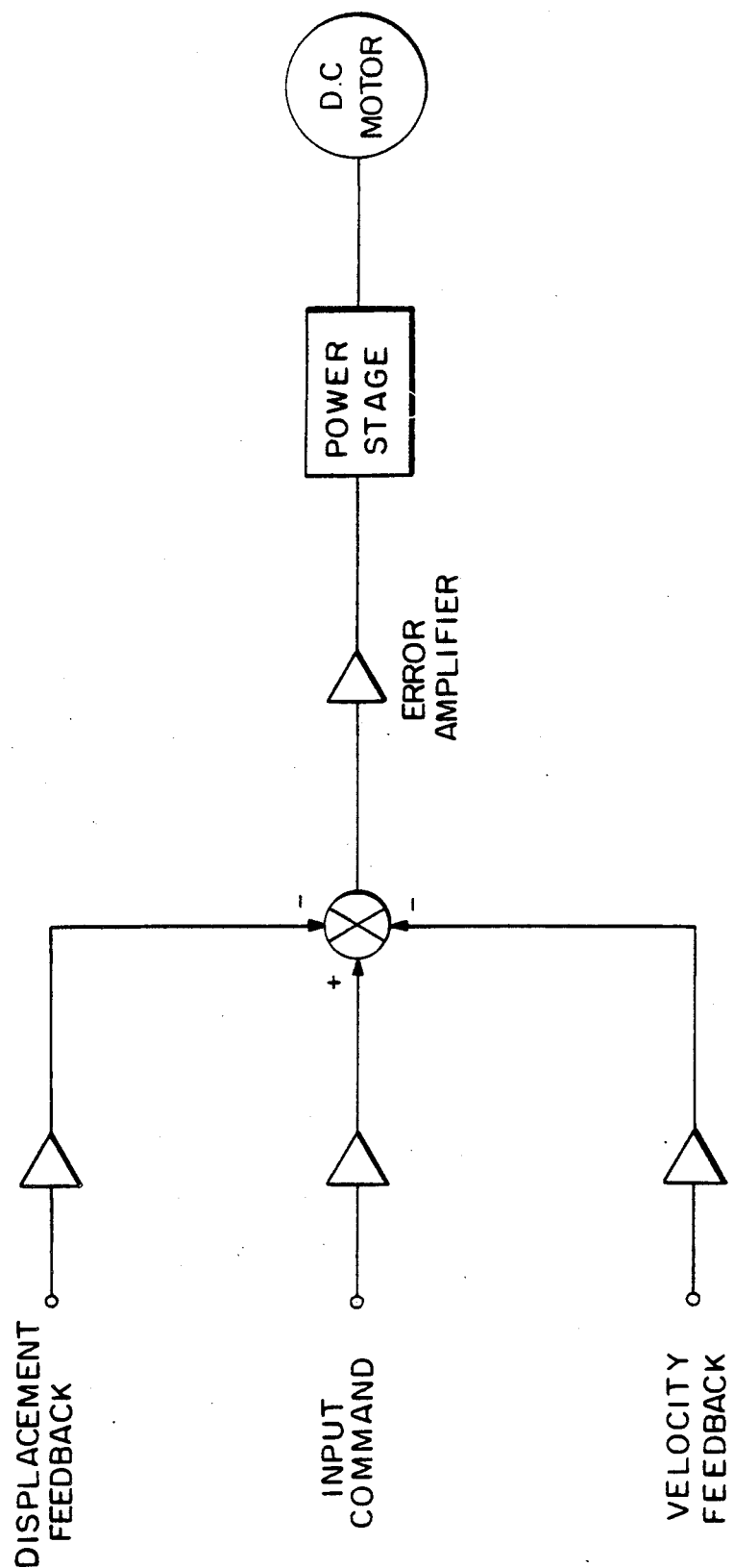

HEART ASSIST DEVICE

STATUS OF APPLICATION

The present patent application is a continuation-in-part application of U.S. patent application Ser. No. 07/304,854 filed Jan. 30, 1989, now abandoned.

FIELD OF THE INVENTION

The invention relates to the field of support of blood circulation in case of acute heart failure and more particularly, to physiological control means of such a device.

Means are provided by which the cardiac system is used to activate the device, integratively with the heart. Thus both elements, the heart and the mechanical device produce an as close as possible response to that expected by the body's controls via its physiological feed-back loops.

The invention is further related to of a device which utilizes physiological data to control its activities, in order to arrive at the correct required blood flow.

BACKGROUND OF THE INVENTION

The cardio vascular system is made up of three main sections:

a. The Heart: the driving organ which provides the exact amount of blood momentarily required, it provides strokes of blood which are energy loaded, in a governed rate and shape.

b. The Vascular bed: This is the distribution system of the blood to the various organs, in accordance with the specific needs of each of them. It also acts as collecting system and general reservoir for blood, towards its reallocation to the heart, to be distributed on a beat by beat basis, in accordance with the integrated needs of the entire body.

c. The control: The control system is made up of subsystems which control the various organs via feed-back loops. All these controlled loops are part of the Central Nervous Systems (CNS), where they are evaluated and integrated. The CNS then operates the vascular flow towards the heart to provide the exact amount of blood to be circulated on the next beat and activates the heart to provide that volume of "blood stroke" at a predetermined rate and shape.

The heart's ventricles are operated by the following parameters, which are governed by the heart's own control system:

1. Preload: the pressure of the atrium preceding the acting ventricle, which defines the volume of the next stroke;
2. Afterload: the "pressure head" against which the ventricle has to act;
3. Contractility: the capability of the myocardium (the heart's muscle) to apply the needed force to reach the required stroke;
4. Rate the heart's beats per minute which together with the stroke volume define the cardiac output.

The coordinated performance of all these above operators is manifested in the Cardiac-Output, which provides the amount of blood per beat, at the right pressure wave.

In case of heart failure, the entire flow system is disturbed. Such disturbance is manifested by an inadequate Cardiac Output and damming of blood behind the defective heart chambers.

Depending on the kind, rate of development, and severity of the heart failure, a whole set of compensating mechanisms is activated in the vascular system by its control system, reallocating and affecting pressures, directing the reduced flow to the various organs, bringing the whole vascular system to a new balance point. This new balance point is in accordance with the central control system, operating the heart's controls as well.

However, in acute heart failure (such as acute myocardial infarction, AMI) a reduction in cardiac output and acute damming of blood behind the affected ventricles occurs. This effect might be too big to be regulated by those compensatory mechanisms and thus be fatal.

If all conventional therapeutic treatments of the heart failure mechanical support of the heart and circulation is required, and more specifically, Ventricular Assistance.

This form of sustained life assist might either be temporary or permanent.

A temporary heart assist system can, for example, be applied to patients who cannot be resuscitated (such as at AMI, or the end of an open heart operation) while recovery of the ventricular function is anticipated. If this does not happen, the device serves as a "bridge to transplantation" until a donor heart will be available.

The permanent ventricular assistance should be applied to patients who sustain permanent damage, where recovery is not anticipated, and the patient is not a candidate for heart transplantation, for any reason.

CURRENT STATE OF DEVELOPMENT OF THE HEART ASSIST SYSTEM (HAS)

The basic principle of a mechanical assist device is the unloading of the defective ventricle of accumulated blood, and pumping it back into the circulation shunting the defective heart.

Evaluation of the data concerning the various models of heart Assist Systems (HAS) show their main drawback to be the discrepancy between the control systems of the body and that of the assist system. See Unger, Assisted Circulation 2, Springer-Verlag 1984 pp 391.

All devices, although providing blood to sustain the perfusion, operate in an independently controlled mode, (in spite of various physiological triggerings) not coordinated with the body's own controls. They lack the capacity to respond to the continuously changing requirements imposed by the body on the heart via pathways, including the central nervous system (CNS), thus leading to the above mentioned discrepancies.

The control systems of the current devices produce either a non physiological flow module where the blood is pumped into the circulation even during the diastolic phase of the heart beat, by using a centrifugal or a roller pump (see Pieronne et al. U.S. Pat. No. 4,622,355 of May 5, 1987), or engage the control of plural parameters of more than one physiological "control-loop" which by themself act independently (see Kurtz et al. U.S. Pat. No. 4,231,354 of Nov. 4, 1980). It has been well established that interconnection of independent "control-loops" (such as the mechanical HAS the body's controlled heart) can not be balanced and would cause, in the long run, the breakdown of one of the interlocked systems, even if coordinated via some common operators. They have continuously tried to rectify the ever changing discrepancies between the "orders" and "responses" on each of them which is based of different and independent algorithems.

Attempts of the CNS to rectify such discrepancies through various routes via other organs, such as the vascular system, kidneys or even the heart itself, may lead eventually to their failure.

SUMMARY OF THE INVENTION

The invention relates to means by which a heart assist system can be integrated with the cardiac system, to be activated in accordance with the body's demands. The system of the invention continually measures one singular parameter which defines the demand for blood to be provided by the heart.

The reading of the entire Arterial Pressure Function during the diastolic phase of the heart-beat provides this singular datum. This function, if utilized as the control parameter when compared to predetermined function serves as the operating function of the assist system. The system evaluates, on a real time basis, the actual performance of the defective heart, calculating the discrepancy between the demand for blood from the heart and the amount actually provided as it is manifested in the atrial pressure. The system continuously commands the HAS to draw the remnant blood from the heart during the diastolic phase thus providing a new artial pressure which corresponds to a predetermined pressure curve. It then supplies the blood during the systolic phase of the same beat.

The sum of the two blood flows—that of the failing heart and, that of the complementary amount pumped by the HAS during the systolic phase—on a real time basis, produces hemodynamic functions which are as close as possible to those expected by the "feedback control loops" of the heart.

DESCRIPTION

The invention relates to a device comprising means which continuously monitor actual heart activities, and applies the data to a heart assist device, the novelty being the ability to integrate these with the biological control system. This is a device capable of providing the physiological rates and pressure shapes of the natural healthy heart.

BRIEF DESCRIPTION OF FIGURES

The invention is illustrated with reference to the enclosed schematical drawings, not according to scale, in which:

FIGS. 2A and 2B—illustrates the device and connection to the patient;

FIG. 8—is a block diagram of an internal servo-loop.

CENTRAL NERVOUS SYSTEM (CNS) (THE "CONTROLLER")

Figure 1:
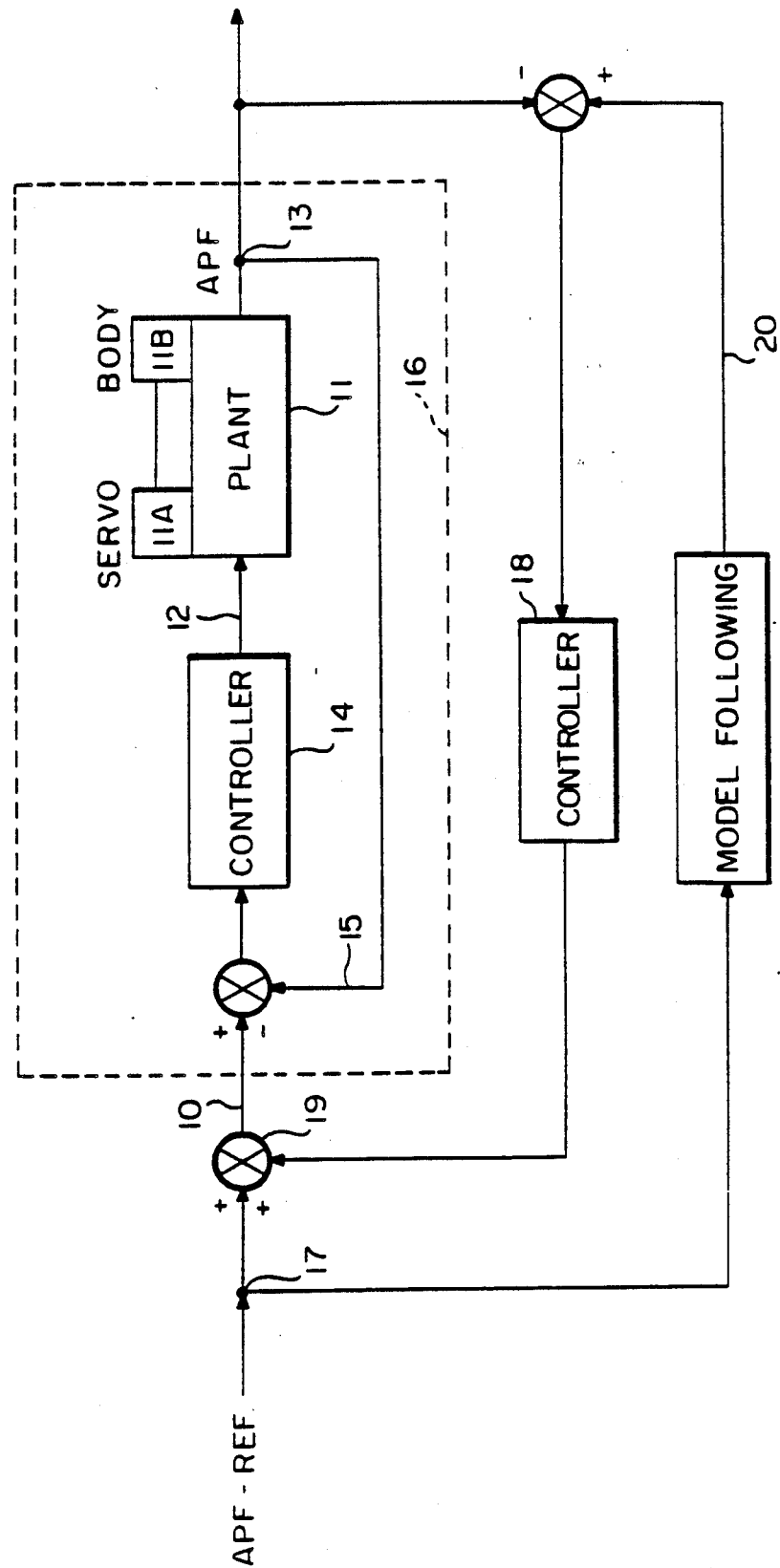
FIG. 1—is a block diagram of the control loop of the system.

The healthy heart (the Active Pumping Element of the "Plant") receives its activating signals via various routes of the Central Nervous System (CNS), (the "Controller" of the body). Evaluation of the monitored data against "reference" data enable the production of signals which activate the natural heart so as to arrive at the correct values of strokes, at the correct shape and timing.

The severely damaged heart, is unable to produce such strokes, causing pathological consequences.

The system of the invention utilizes the whole Atrial Pressure Function (APF) during the diastolic phase of each heart beat to serve as reference of the required assist.

The blood flows, towards the heart, either veinous blood to the Right Atrium or oxygenated blood from the lungs via the pulmonary artery to the Left Atrium.

Those two flow rates are not always equal as they are part of the controlled cardiovascular system. If we take as an example the Left Atrium, the filling blood flow is building up the pressure pattern of the atrium. During the systolic phase of the heart beat, while there is no flow from the atrium to the proceeding ventricle, the pressure is building up during the diastolic phase, the blood is emptied into that ventricle and the pressure drops accordingly. It has been established that even if the pressure built up during the systolic phase is changing, because of larger amounts of blood flow towards the heart during that period, the pressure drops during the diastolic phase and remains quite constant, meaning changes in stroke volumes, controlled and operated by the CNS via the known "operators" described above.

We utilize this route as the way to combine our HAS with that of the body.

A pressure function which represents the pressure in the atrium, had it functioned properly, is fed into the system. We provide the means to interlock our device with the rate of the heart, to draw blood during the diastolic phase in the amount which reduces the measured atrial pressure from the pathological level to the predetermined level which should exist at that moment, in real time rates. Such a pressure function is accepted by the body's controls being in the correct shape and response with the CNS's function, having a shift from the real function as defined for each individual.

Such constant discrepancies are known to be accepted by closed loop controls, regarded as "regular heart failure" within the limits of the cardiovascular system, calling to particular responses via one of the routes of the system vaso-constriction, dilatation or one of the related organs such as the liver, kidney, lungs or the heart.

Whereas any other controller, which affects the shape as well as the shift will provide entirely confusing signals to the controller of the feed-back, causing utter confusion, which, in the attempt to rectify the continually charging signals, via continuously different routes which is the "proper" response for each of them at the time, causing at the end the failure of the system. This knowledge of the theoretical consideration of the interaction of two differently activated controls which act on one "plant" applies to the body-device controls as well.

The device of the invention utilizes the entire Atrium Pressure Function (APF) during the diastol phase of the heart beat as the reflection of the activating signals for "Pumping Element of the Plant", the heart.

The APF is a unique legible function which reflect the evaluated data of the CNS. This function is the expression of the amount of blood directed towards the atrium by the vascular system; the predetermined tonus of the atrium myocardia; the contraction of the atrium and the heart rate, all of which are monitored by the CNS.

A physiological feed-back loops which comprises a "Controller" which contours a Reference APF predetermined by the CNS and in which a system is constantly receiving inputs from the APF is capable of controlling the heart as known to us. Evaluating the difference between these functions, may arrive at activating-signals which may cause the heart to act (draw and pump blood) in a way which produce the proper APF.

Changing demands for blood, in accordance with changing needs of the body, should result in changes in blood flow towards the heart, and/or the atrial myocardial tonus, and/or contraction forces of the atrium, and/or rate of heart beat, all of which are manifested in the APF. The "Controller" activates the ventricle to respond, in accordance with the "Ref . APF", thus providing the changing Cardiac-Output, during the daily life cycle.

As mentioned above, in sudden acute heart failure, the "Pumping Element" is suddenly disrupted. It can no longer respond to the "signals" of the "Controller". This disturbance is manifested in a pathological APF.

According to this model, means are provided whereby an assist device can be integrated with the body's control system. The system comprises a pump connected to the heart. The activating controls of the pump measure the APF of the heart, evaluate it against a predetermined Reference APF, and activate the sensitive-servo-driven means, capable of drawing and pumping the excess blood accordingly, to arrive at the correct APF.

The system based on the invention can be used as an activating system for the Artificial-Heart, Left, Right or Biventricular Assist, for permanent or temporary applications.

The invention is illustrated with reference to the enclosed FIGS. in which the schematic block diagram (FIG. 1) illustrates the principle of a system for use with the failing ventricle. Block 11 (the Plant) between the points 12 and 13 (which defines the patient and the pumping devices) contains the dynamics of the patient 11B and the assist system 11A. The latter contains a servo-mechanism which receives its signals from the Controller 14, and activates the pumping element of the assist system accordingly.

This controller may use for example recursive equations such as the following one:

$$Y_{(n)} = [(A_1 Y_{(n-1)} + A_2 Y_{(n-2)} + A_3 Y_{(n-3)} + A_4 Y_{(n-4)}) + (B_0 V_{(n)} + B_4 V_{(n-1)} + B_2 V_{(n-2)} + B_3 V_{(n-3)} + B_4 V_{(n-4)})] \cdot K$$

where:
A and B = constants
Y = controller 14 Output
V = controller 14 input
K = gain
n = current number of computer samples.

Block 14 designates the control elements of the central loop, within the dotted lines 16. This block receives the signals of the predetermined Reference Atrium Pressure Function (APF Ref.) at point 17, and the existing Atrial Pressure Function (APF) (which is recorded at point 13) at point 15.

This controlled closed loop system (16) thus contains the patient who has his own individual dynamic response. As the dynamic response is very much individual, depending on the patient's own internal parameter such as size, weight, age, classification blood vessels etc. No general equation can be composed as to the dynamic parameters of the feedback controller of the pump in order to arrive at the exact and correct response at point 13. Correcting factors added in an additional "Model-Following" (MF) loop, affects directly the parameters of the Reference APF. The controller of this loop 18 receives the difference between the signals of the real APF, and those required, according to the Model at point 20, and then produces corrected signal at point 19 which causes the proper APF.

The difference between the signals of the measured APF (at point 13) and those expected (20) according to the "MF" block, is gained at the controller block 18 which produces a correction signal at point 19.

The correction signal is added to the APF-Ref. at point 19 to produce another APF-Ref. signal at point 10. The signal is the input to the controller (14) adapted to the specific patient.

The "MF" block together with controller 14 enable the compensation and adjustments to changes in accordance with the body's dynamic response by considering the body's reaction.

The "MF" block may, for example use the following recursive equation, to produce that data.

$$W_{(n)} = D[W_{(n-1)} + RAPF_{(n)} + RAPF_{(n-1)}]$$

when
D = constant
W = block MF output
RAPF = Reference Atrium Pressure Function.

The invention is further described by way of illustration only, in its application as a temporary left Ventricular Assist device (LVAD). The device is schematically described in FIG. 2 in which the LVAD, 21, receives the monitored left APF and ECG, 22, of the patient, 23, which are fed into the microprocessor on the main computer PCB, 24. The microprocessor also times, according to a built in algorithm the cycle of the pump of the device, (the diastol-suction periods). The APF is evaluated by the microprocessor against a Reference APF predetermined for the specific patient, which is fed into the computer PCB 24 via the panel 26 of the device.

The summation of the evaluated data is sent as an electrical signal to the activating servo-mechanism of the variable pulsating blood pump (26, servo-amplifier and 27, the servo-mechanism of FIG. 2).

Figure 7A:
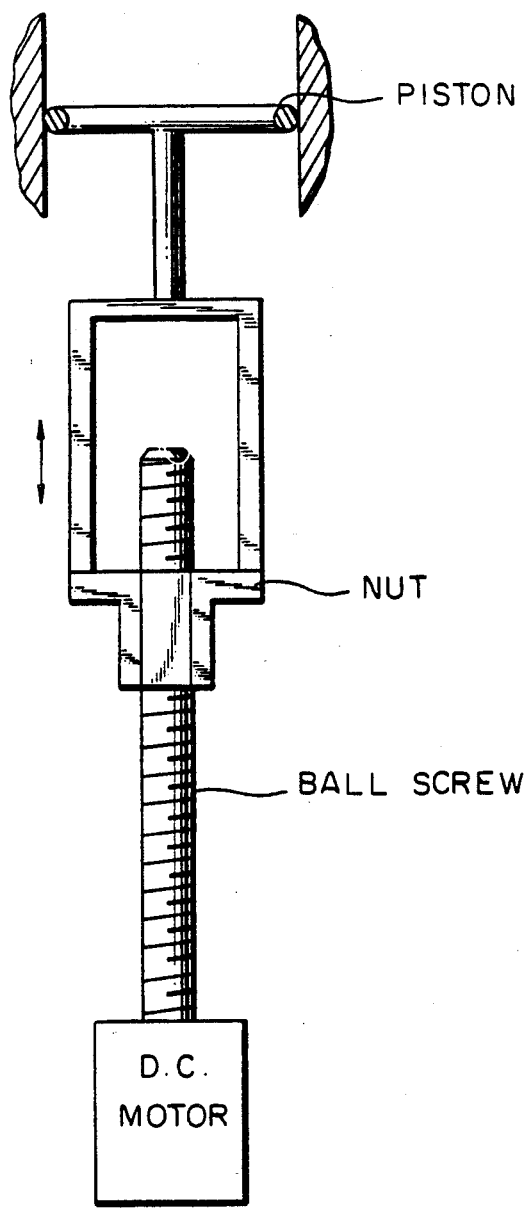
FIGS. 7A and 7B—illustrates a variable pulsating pump and a typical displacement curve obtained thereby.
Figure 7B:
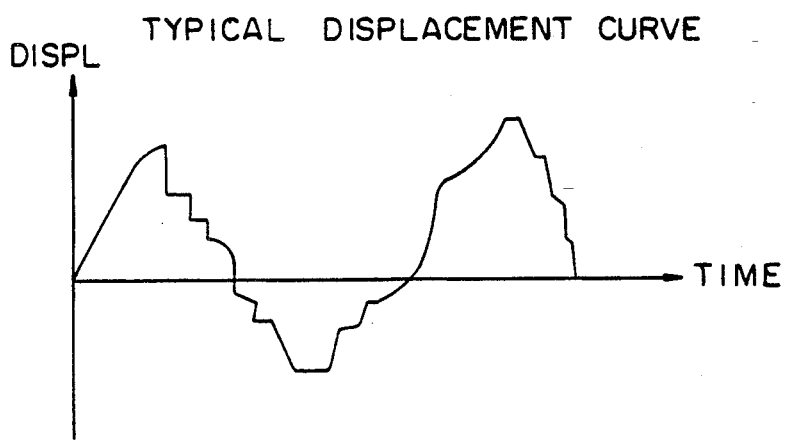

The variable pulsating pump may be way of example contain a quick response D.C. motor coupled with a ball screw and piston, as well as displacement and speed measuring devices (FIG. 7).

The internal servo loop receives the displacement signal from the computer, that evaluates the heart performance as explained in FIG. 1, and moves the piston up or down to eject or suck blood activated by its servo-mechanism.

Activating servo-mechanism has internal control loops of its own as shown in FIG. 8. These loops produce the controlled movements of the piston 28 (of FIG. 2) which activated the "Pumping Head", 29.

This pumping head is drawing blood out of the heart during the diastolic phases of the beat and pumping it back during the systolic phase of the same beat, to provide, together with the heart, the required stroke volume.

The space between the moving piston and the diaphragm of the blood pumping head, is fluid-filled assuring accurate and proper responses to any tiny movement of the system 28.

A new displacement signal is given every few milliseconds, on the internal servo control loop forces the piston to move up or down according to the signal, assuring smooth and accurate action, preventing overshooting and negative pressure in the stream (FIG. 8). This movement may change many times in amplitude and direction within one heart cycle thus enables a real time control over the controlled APF.

Figure 3A:
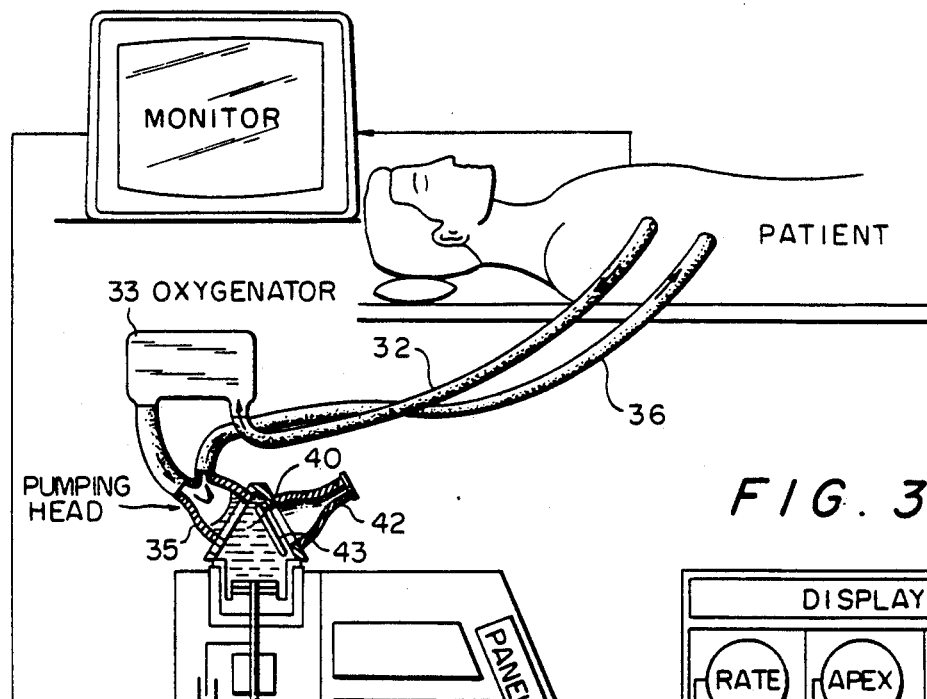
FIGS. 3A and 3B—illustrates the use of the system as a heart lung machine.
Figure 3B:
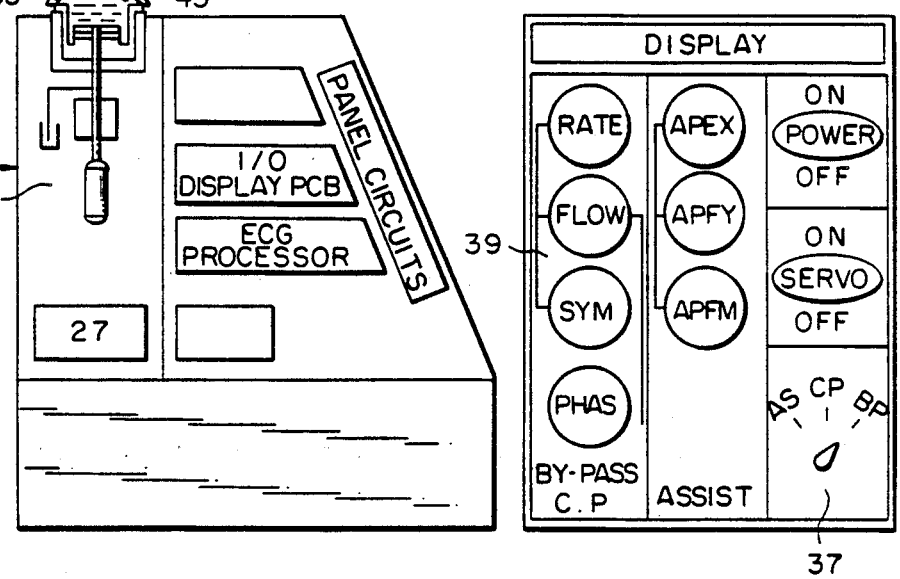
Figure 4A:
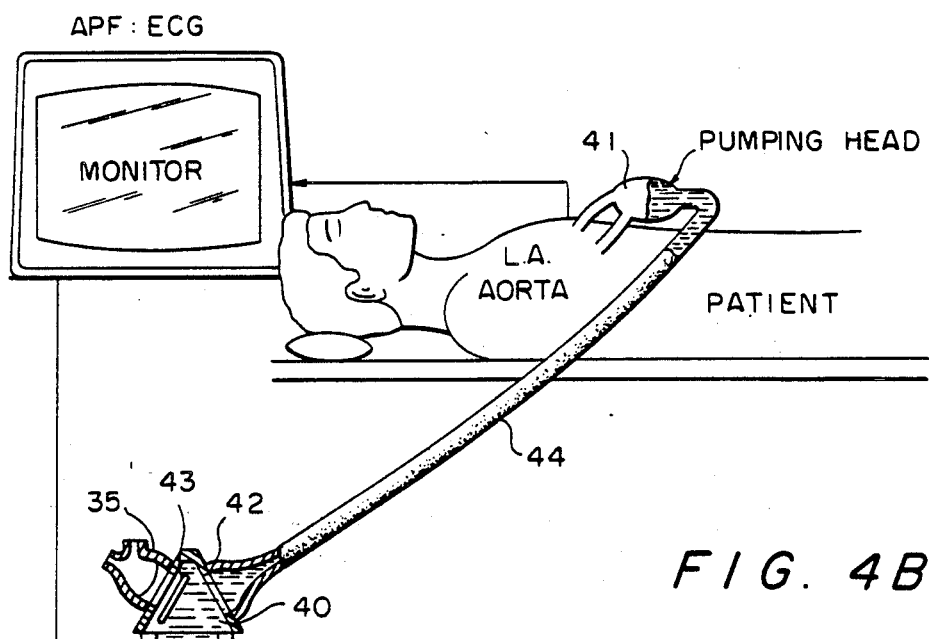
FIGS. 4A and 4B—illustrates a further embodiment of the use of the system as a heart lung machine.
Figure 4B:
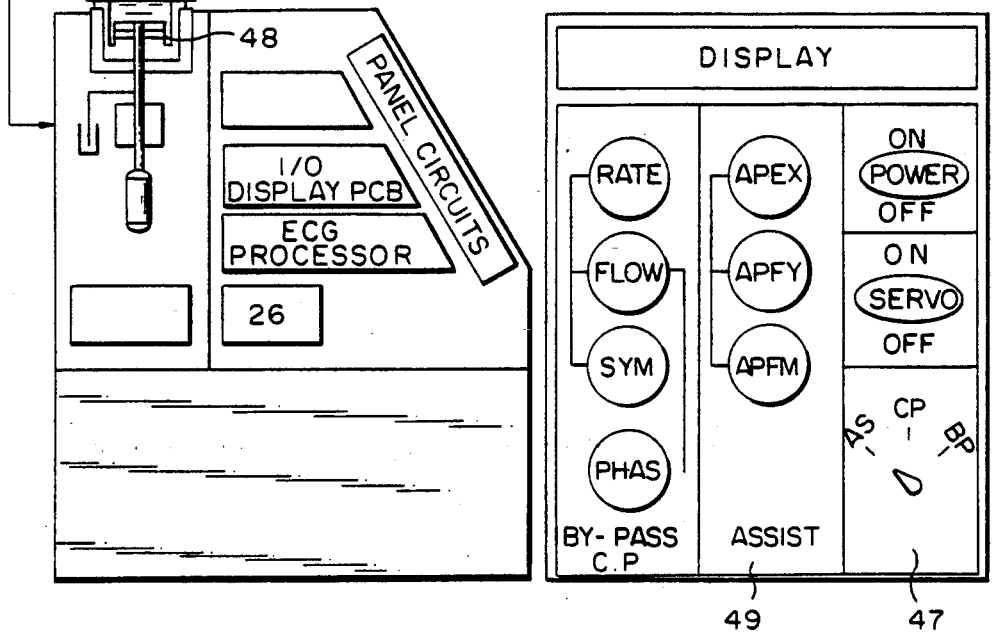

A working example of the application of the invention as a multiple blood pump, integrated in a Heart-Lung-Machine (HLM), is shown in FIGS. 3 and 4. The pulsating HLM is used for Cardio-Pulmonary By-Pass (CPY) during heart surgery (FIG. 3).

Blood pump, integrated in a Heart-Lung-Machine (HLM), is shown in FIGS. 3 and 4. The pulsating HLM is used for Cardio Pulmonary By-Pass (CPU) during heart surgery (FIG. 3).

At this mode of operation the blood flows from the patient 31, via the venous line 32, to the oxygenerator 33. From the oxygenerator, the blood is drawn by the hydro-electro-mechanical pump, 34, (described in FIG. 2), via a "CPB Disposable Blood Pumping Head", 35, (which will be described in FIG. 6), and pumped back to the patient through the arterial line 36.

This application provides an HLM with the capabilities of providing at will, rates, systole/diastole, pulse shape, stroke volume, dp/dt of the pumped blood, arriving at desirable blood pressures during the cardiopulmonary by-pass, thus providing the surgeon the ability to produce and control all these parameters.

At will, during partial By-Pass or at the critical stage of disconnecting the patient from the HLM ("wearing off"), our system enables synchronization of the pulsating pump to the patient's ECG, providing via the panel 37 a desirable systolic/diastolic wave, with shapes, which can produce the therapeutic "counter-pulsation" (C.P.) effect.

If desire all efforts, the patient needs assistance, the system is turned into an Assist Device.

Figure 5A:
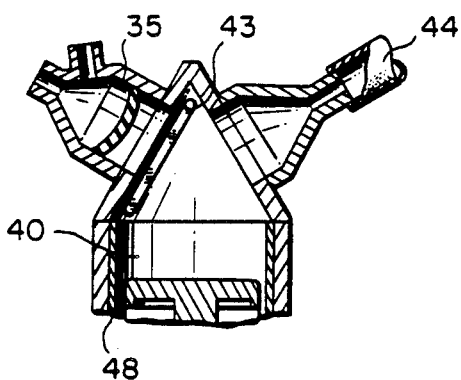
FIGS. 5A and 5B—illustrates a "Flow-Directing Component"
Figure 5B:
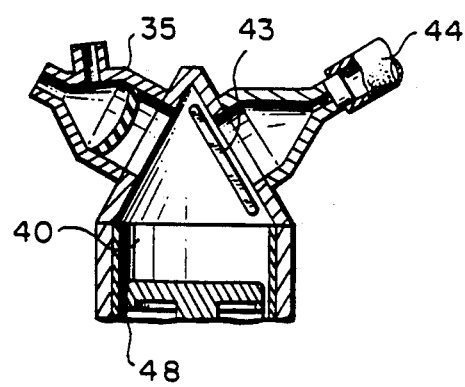

The patient remains connected to the Bypass mode, while the surgeon carries out the necessary surgical operations to enable the connection of the "Assist Disposable Blood Pumping Head", 41, in FIG. 4, and the filling of the hydraulic line 44, connecting the Pumping Head to the hydraulic "Flow Directing Component 40 of FIGS. 4 and 5".

This "Flow Directing Component" described in FIG. 5, is set above the pumping piston 48. It comprises a "CPB" disposable Blood Pumping Head, 35, mounted on one side, and a fluid filled cone and line, 44, on the other side. A tilting disc, 43, within this component, can be turned from position (a) for the device to be operated as HLM and C.P., to position (b), turning it to the Assist mode positioning the knob 37 on the panel of FIG. 4, to the Assist position operating the device. The CPB Disposable Head, 35, is disconnected and the patient leaves the Operating Room while still connected to the device which operates on its own power supply.

As the patient recovers, the procedure is reversed and he is disconnected from the device.

Figure 6A:
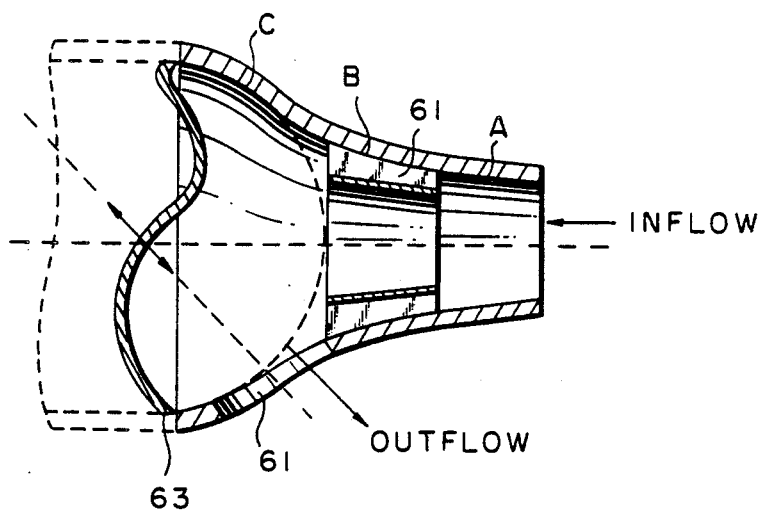
FIGS. 6A, 6B and 6C—illustrates a blood pumping head.
Figure 6B:
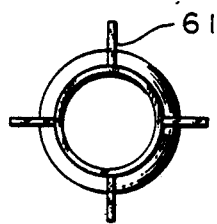
Figure 6C:
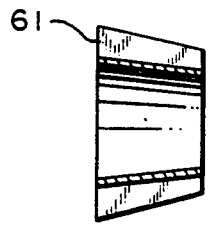

The "Disposable Blood Pumping Head", 35, in FIGS. 3 and 4, 29, in FIG. 2, and 41, in FIG. 3, are described in detail in FIG. 6. It is designed to reduce blood hemolysis caused by turbulent flows. This is achieved by a diverging cone of the entrance zone (A) of the "Head" with the addition of the diffuser 61, which is inserted in the larger conical zone (B) of the funnel. It enables further reducing of the flow velocities along a short distance, thus reducing excess turbulence, shear stresses and energy dissipation.

The direction of the outflow, 52, within the spherical zone (C), is coordinated with the moving membrane, 63, to bring about a better washout of the blood from the "Head" at each stroke in order to avoid blood particle sedimentation.

The operation of the device is illustrated with reference to FIGS. 3 to 5 of the enclosed drawings.

The device is located in the operating theater (O.R.) and is used instead of one of the pumps which comprise the heart-lung machine (HLM) and the mode of operation is as follows:

I

Preparation Stage

The perfusionist connects the pumping head 35 which includes inlet and outlet valves to the flow-directing member 40.

The pumping head is connected to oxygenator 37 while the tilting disk 43 is kept to the right disconnecting the assist flow direction; and the space in the flow directing device 40 is filled with hydraulic fluid. The procedure of connecting the patient to the device is according to standard protocol of use of a heart-lung machine (HLM) on a cardiovascular bypass.

II

Bypass Stage

As the patient is on bypass, while his heart is beating, the operating knob 37 is positioned on CP and the perfusionist starts perfusing blood by turning the FLOW and SYM knobs 39 on the panel, to reach the desired flow rate and pressure. At the "Cross Clamp" stage of the operation, when heart beat is stopped, the perfusionist turns the knob 37 to the CP position, enabling him to operate the RATE (beats per minuts), FLOW (liters per minute) and SYM (arterial pressure) by means of 39, as required by the surgeon. At the end of the operation when the heart starts beating again, the perfusionist turns knob 37 back to the CP position, weaning the patient off the bypass by reducing FLOW accordingly and the patient is disconnected from the HLM.

III

Counterpulsating

At the weaning stage, the surgeon has the option to apply a counterpulsating mode to overcome possible difficulties of the heart in maintaining circulation. In this case, the patient is kept connected with the device while the perfusionist turns PHASE knob 39 which applied counter-pulsating pressures and flows, which are intended to improve the performance of the heart.

IV

Assist Mode

If in spite of such measure carried out in accordance with standard protocol, the condition of the patient fails to improve, and it is still impossible to disconnect him from the HLM, the surgeon has to cannulate the left atrium or ventricle. The perfusionist prepares the Assist Pumping Head 41 connecting it via the hydraulic line 44 to flow directing device 40 and the hydraulic line 44 is filled with hydraulic fluid.

The pumping head 41 is connected on the inlet side to the left atrium or ventricle; on the outlet side to the aorta, and on the rear side to the hydraulically propelling line 44. At this stage, the LAF is determined via knobs APEX, APFY, APFM, 49, in accordance with the instructions of the surgeon.

V

The Final Stage

The connected, assisted patient leaves the operating room while he is connected to the assist device of the invetion and moved to an intensive care unit (ICU). As soon as the condition of the patient improves and no assist device is required anymore, the patient is again moved to the operating room and the device is disconnected.

We claim:

1. A heart assist system for connection to a patient who needs an augmented blood supply, said system comprising:
   means for drawing blood from said patient and for pumping said blood back to a circulatory system of said patient;
   means for continuously monitoring the artial pressure function of said patient;
   computing and data storing means for storing predetermined values defining a curve of defined artial pressures;
   means for continuously calculating the instant difference between said atrial pressure of said patient and said predetermined values;
   means for activating said means for drawing and pumping blood to adjust said atrial pressure to a predetermined value of said values;
   means for controlling on a real time basis the quantity of blood drawn during the diastolic phase of the heart beat of said patient and blood supplied to the patient during the systolic phase of the heart beat of said patient.

2. A heart assist system according to claim 1, comprising:
   means for continuously monitoring the atrial pressure function and means for continuously comparing the difference between the values of the actual instant measurement values with the values of the reference atrial pressure function, thus establishing the blood supply requirements of the patient at any instant.

3. A heart assist system according to claim 1, wherein said means for drawing and pumping blood comprises a variable pulsating pump.

4. A heart assist system according to claim 3, adapted for use in conjunction with, and as a pulsating controllable pump for a heart lung machine.

5. A heart assist system according to claim 3 adapted for use as a counterpulsating pump at the weaning off stage of a heart operation.

6. A heart assist system according to claim 1 adapted for connection to a patient for a prolonged period of time until recovery of the heart or as a bridge to heart transplantation until a donor heart becomes available.

* * * * *